US006748264B2

(12) United States Patent
Chai

(10) Patent No.: US 6,748,264 B2
(45) Date of Patent: Jun. 8, 2004

(54) BODY FAT ANALYZER WITH INTEGRAL ANALOG MEASUREMENT ELECTRODES

(75) Inventor: Sunny Chai, Hong Kong (HK)

(73) Assignee: Fook Tin Technologies Limited, Hong Kong (CN)

( * ) Notice: Subject to any disclaimer, the term of this patent is extended or adjusted under 35 U.S.C. 154(b) by 38 days.

(21) Appl. No.: 10/067,039

(22) Filed: Feb. 4, 2002

(65) Prior Publication Data

US 2003/0149374 A1 Aug. 7, 2003

(51) Int. Cl.[7] .................................................. A61B 5/04
(52) U.S. Cl. ...................................................... 600/546
(58) Field of Search ................................ 600/546, 300, 600/547, 407, 506, 507; 428/697, 432, 469, 472, 673, 699, 701, 702; 427/376.2, 164; 156/102

(56) References Cited

U.S. PATENT DOCUMENTS

| | | | |
|---|---|---|---|
| 4,949,727 A | 8/1990 | Yamazaki et al. | 128/734 |
| 5,122,391 A | 6/1992 | Mayer | 427/126 |
| 5,279,851 A | 1/1994 | Minosou et al. | 427/126 |
| 5,296,122 A | 3/1994 | Katsube et al. | 204/298.04 |
| 5,458,753 A | 10/1995 | Sato et al. | 204/192.29 |
| 5,538,905 A | 7/1996 | Nishioka et al. | 437/24 |
| 5,578,248 A | 11/1996 | Hattori et al. | 252/518 |
| 5,605,610 A | 2/1997 | Ishibashi | 204/192.29 |
| 5,611,351 A | 3/1997 | Sato et al. | 128/734 |
| 5,628,933 A | 5/1997 | Carter et al. | 252/518 |
| 5,652,062 A | 7/1997 | Cava et al. | 428/426 |
| 5,736,267 A | 4/1998 | Mitsui et al. | 428/702 |
| 5,844,175 A | 12/1998 | Nakanishi et al. | 178/18.03 |
| 5,966,580 A | 10/1999 | Watanabe et al. | 419/9 |
| 5,993,973 A | 11/1999 | Lee et al. | 428/433 |
| 6,086,790 A | 7/2000 | Hayashi et al. | 252/500 |
| 6,146,765 A | 11/2000 | Mitsui et al. | 428/428 |
| 6,151,523 A * | 11/2000 | Rosell Ferrer et al. | 600/547 |
| 6,188,925 B1 | 2/2001 | Kawanishi et al. | 600/547 |
| 6,208,890 B1 | 3/2001 | Sarrazin et al. | 600/547 |
| 6,221,520 B1 | 4/2001 | Takaki et al. | 428/699 |
| 6,243,651 B1 | 6/2001 | Masuo | 702/19 |
| 6,249,082 B1 | 6/2001 | Fukuyoshi et al. | 313/479 |
| 6,256,532 B1 | 7/2001 | Cha | 600/547 |
| 6,308,096 B1 | 10/2001 | Masuo | 600/547 |
| 6,313,571 B1 | 11/2001 | Hasegawa et al. | 313/309 |
| 6,315,848 B1 | 11/2001 | Kondo | 156/99 |
| 6,315,874 B1 | 11/2001 | Suzuki et al. | 204/192.29 |
| 6,320,204 B1 | 11/2001 | Hirabayashi et al. | 257/71 |
| 6,320,309 B1 | 11/2001 | Nomura et al. | 313/495 |
| 6,320,629 B1 | 11/2001 | Hatano et al. | 349/15 |
| 6,321,112 B1 | 11/2001 | Masuo | 600/547 |
| 6,336,045 B1 * | 1/2002 | Brooks | 600/547 |
| 6,541,133 B1 * | 4/2003 | Schicht et al. | 428/697 |
| 2001/0014777 A1 | 8/2001 | Serizawa et al. | 600/547 |
| 2002/0172775 A1 * | 11/2002 | Buhay et al. | 427/376.2 |

FOREIGN PATENT DOCUMENTS

| | | |
|---|---|---|
| EP | 1 125 550 A1 | 8/2001 |
| JP | 2000-225102 | 8/2000 |

OTHER PUBLICATIONS

U.S. patent application Ser. No. 09/968,727, Chai et al., filed Oct. 1, 2001.
U.S. patent application Ser. No. 60/284,228, Chai, filed Apr. 16, 2001.
U.S. patent application Ser. No. 60/284,541, Chai, filed Apr. 17, 2001.
"Subtractive Thick Film Technology" in http://www.silonex.com/ceratel/stf.html (last modified Feb. 12, 2001).
"The Evolution of Thick Film" by Andy London and Dr. Jerry Steinberg in http://www.4hcd.com/techpprs/evoltf/index.html (1997).
"Resistor Technology" in http://www.4hcd.com/docs/HEN202.htm (last visited Jan. 2, 2002).

* cited by examiner

Primary Examiner—Max F. Hindenburg
Assistant Examiner—Brian Szmal
(74) Attorney, Agent, or Firm—Jones Day

(57) ABSTRACT

A body fat analyzer having integrated measurement electrodes is disclosed. The assembly comprises a substrate; at least two conductive-film electrodes formed from a conductive material integrated on the substrate and capable of contacting a body to be measured; and a measurement circuit electrically connected to the electrodes. There is further disclosed a water-resistant body fat analyzer that comprises a substrate having top and bottom surfaces and an edge therebetween; at least two electrodes in contact with the top surface of the substrate, and capable of contacting an object having a biometric electrical characteristic to be measured; and a body fat measurement circuit mounted below the substrate and electrically connected to the electrodes such that the top surface of the substrate remains intact, whereby water present thereon is prevented from reaching the circuit. The invention is further directed to methods of manufacturing the disclosed body fat analyzers.

11 Claims, 7 Drawing Sheets

BODY FAT ANALYZER WITH INTEGRAL ANALOG MEASUREMENT ELECTRODES

FIELD OF THE INVENTION

The present invention relates generally to a biometric data acquisition assembly, and more particularly to a body fat analyzer having measurement electrodes made from a conductive film integrated on a substrate. It further relates to a water-resistant body fat analyzer having electrodes mounted on its upper surface and connected to measurement circuits within the analyzer without requiring perforations in its upper surface.

BACKGROUND

Percent body fat has long been recognized as a useful indicator of a person's health. One technique that has been developed to measure a person's percent body fat is the so-called "bioelectrical impedance" technique. According to this technique, a person's body fat is measured by determining the impedance of the person's body to electrical signals, and calculating the percent body fat based upon the measured impedance and other variables such as height, weight, age, and sex. Body impedance is typically determined by supplying a constant current through at least two electrodes that contact the body, thereby causing a voltage to develop across the body. This voltage is measured either (1) via the same electrodes through which current is supplied, or (2) via one or more pairs of voltage-measuring electrodes. The body impedance is then readily calculated from the current and the measured voltage, and the percent body fat is in turn calculated from the body impedance.

Although many body fat analyzers based on these techniques are currently available in the retail market, they tend to have bulky electrodes, to be susceptible to damage from water, and to be relatively expensive to manufacture. One example of such a body fat analyzer is described in U.S. Pat. No. 5,611,351 and shown in FIG. 1. With reference to FIG. 1, a user stands on four large metal electrodes 2,3, through which current is supplied and the developed voltage measured. The user's weight and height are also measured, by a weight scale within base 5 and height scale 4,4A. The user's body impedance and body fat are then calculated and displayed on display 6. A plan view of base 5 is shown in FIG. 2, and a sectional view is shown in FIG. 3. From these figures, it may be seen that electrodes 2,3 are large, thick, and bulky. Such electrodes are relatively expensive to manufacture, since they require a large amount of raw material and processing. Further from FIGS. 1–3, although the wiring associated with electrodes 2,3 is not directly indicated, they appear to be connected to the measurement and display circuitry 6 via conductors that pass through openings in the upper surface 1 of base 5. These openings may disadvantageously permit water and dust to enter base 5. Moreover, despite the size of electrodes 2,3, the user is required, by their geometry and by heel guides 7, to place his feet in very specific locations, which may not be comfortable for users of different body types. Finally, since electrodes 2,3 alone support the user's weight, he may feel some discomfort as the electrodes press into his feet.

A more recent bioimpedance body fat analyzer, described in U.S. Pat. No. 6,308,096 and shown in FIGS. 4 and 5, comprises a handheld unit 40 and a base unit 42, connected by a cord 44. The analyzer has eight electrodes, four in handheld unit 40 and four in base unit 42. It may be seen from FIG. 5 that the base-mounted electrodes 50, 52 in this body fat analyzer are relatively small, and flush-mounted in a rubber support 54, itself mounted on a base 56 and held in position by upper layer 58. Although this body fat analyzer is more comfortable to use than that described above, it is still relatively expensive to manufacture because of the large number of manufacturing steps required to mold electrodes 50, 52, mount them in rubber support 54 and then install the assembly in position between base 56 and upper layer 58.

Still another recent body fat analyzer is described in U.S. Pat. No. 6,243,651 and shown in FIGS. 6 and 7. This analyzer is less expensive to produce than those described above, since it is a small, handheld unit having a compact plastic case 60 and four small electrodes 62. Electrodes 62 are made of stainless steel (SUS) sheet metal, which can be produced and installed more easily than the molded electrodes in the analyzers described above. But this analyzer, too, requires manual assembly and thus is still relatively expensive to produce. Additionally, like the analyzers described above, this analyzer is susceptible to damage by moisture that may reach the inside of the unit through openings in the case 60 around the keys 64, display 66, or at the points at which electrodes 62 (or their associated conductors) enter case 60.

SUMMARY OF INVENTION

It is therefore an object of the present invention to provide a body fat analyzer having a reduced risk of damage by environmental factors.

It is a still further object of the present invention to provide a body fat analyzer that may be easily and inexpensively mass-produced.

The inventor of the present invention has accomplished these objectives through the application of conductive-film integration technology to body fat analyzers. Thus, a body fat analyzer in accordance with the invention preferably comprises a substrate; at least two conductive-film electrodes integrated on the substrate and capable of contacting a body to be measured; and a body fat measurement circuit electrically connected to the electrodes.

A problem that arises when such an analyzer is constructed is that conductive-film electrodes have high resistances, e.g., between 1–100 ohms, which affects the measured value of resistance. In accordance with the present invention, this problem is overcome by configuring the body fat measurement circuit to calculate, based upon the measured body impedance, a corrected body impedance value that is independent of the impedance of the electrodes.

The substrate may be composed of any non-conductive material capable of receiving a conductive-film layer. Suitable materials include, e.g., glass, ceramics, plastics, non-conductive stones, and insulators.

The electrodes may be composed of any conductive material suited to application as a conductive film on a substrate, e.g., metals, semiconductors, conductive inks and pastes, and transparent conductive materials such as zinc stannate ($ZnSnO_3$ and $Zn_2SnO_4$), fluorine-doped zinc oxide (ZnO:F), indium tin oxide ($In_2O$:Sn and $In_2O_3$:Sn), titanium nitride ($TiN_x$), and fluorine-doped tin oxide ($SnO_2$:F). In order to minimize material and processing costs while maintaining a suitable conductance, the electrodes are preferably between 20 nanometers to 5 micrometers thick.

Preferably, a body fat analyzer in accordance with the invention further comprises a heating element in contact with the substrate and capable of warming the surface of the analyzer. This warming action renders the analyzer more comfortable to use and may also increase the accuracy of the body fat measurement, since better capillary blood flow at the surface of the foot results. To control the heating element, a current source electrically connected to it is also required. Still more preferably, since the conductive-film electrodes themselves have a relatively high resistance, they may be used as the heating elements, and the current source may be included in the body fat measurement circuit.

In a further embodiment of the present invention, other circuits useful in body fat analyzers may be additionally provided on the substrate as integrated circuits. Such circuits may include, for example, a thin-panel display, a touch-switch keypad, and an electromagnetic shield positioned to protect the measurement circuit. Preferably, the measurement circuit itself is integrated on or under the substrate.

The present invention further includes a method of producing a body fat analyzer, comprising the steps of: (1) forming two or more conductive-film electrodes on a substrate; and (2) electrically connecting a biometric data acquisition circuit to the electrodes. The electrodes may be formed on the substrate by known thin- or thick-film integration techniques, such as sputtering, vapor deposition, photolithography, screen-printing, etc.

The electrodes may be shaped by either of two known techniques: (1) creating a uniform layer of conductive material on the substrate; and selectively removing predetermined portions of the conductive material by, e.g., chemically etching, sand-blasting, laser patterning, or grinding away predetermined portions of the conductive material; or (2) by applying the electrode material only to selected portions of the substrate. Preferably, the method of producing the body fat analyzer further comprises the step of additionally integrating, on the substrate, at least one of (1) a thin-panel display, (2) a touch-switch keypad, (3) a heater element, and (4) an electromagnetic shield.

In another embodiment of the invention, a body fat analyzer having improved water-resistance is provided. It comprises a substrate having top and bottom surfaces and an edge therebetween; at least two electrodes in contact with the top surface of the substrate, and capable of contacting an object having a biometric electrical characteristic to be measured; and a body fat measurement circuit mounted below the substrate and electrically connected to the electrodes such that the top surface of the substrate remains intact, whereby water present thereon is prevented from reaching the circuit. Preferably, the circuit is located below the bottom surface of the substrate and is connected to each of the electrodes via a conductive path traversing the edge of the substrate. To further improve the water-resistance of the analyzer, a gasket is preferably mounted on the substrate that tends to keep water present on the top surface of the substrate from reaching the bottom surface of the substrate.

The invention, in this embodiment, further includes a method of producing a body fat analyzer, comprising the steps of: (1) affixing at least two electrodes on the top surface of a substrate having top and bottom surfaces and an edge therebetween; and (2) electrically connecting the electrodes to a biometric data acquisition circuit mounted below the substrate, such that the top surface of the substrate remains intact, whereby water present thereon is prevented from reaching the circuit. Preferably, the connecting step includes the step of providing, for each electrode, a conductive path from the electrode on the substrate's top surface to its bottom surface via its edge. Finally, the method preferably includes the step of providing, near the edge of the substrate, a gasket that tends to keep water present on the top surface of the substrate from reaching the bottom surface of the substrate.

BRIEF DESCRIPTION OF THE DRAWINGS

A fuller understanding of the present invention may be obtained by reference to the following detailed description and to the drawings, wherein like reference numerals are used to identify similar components in the various figures and in which.

DETAILED DESCRIPTION

Figure 1:
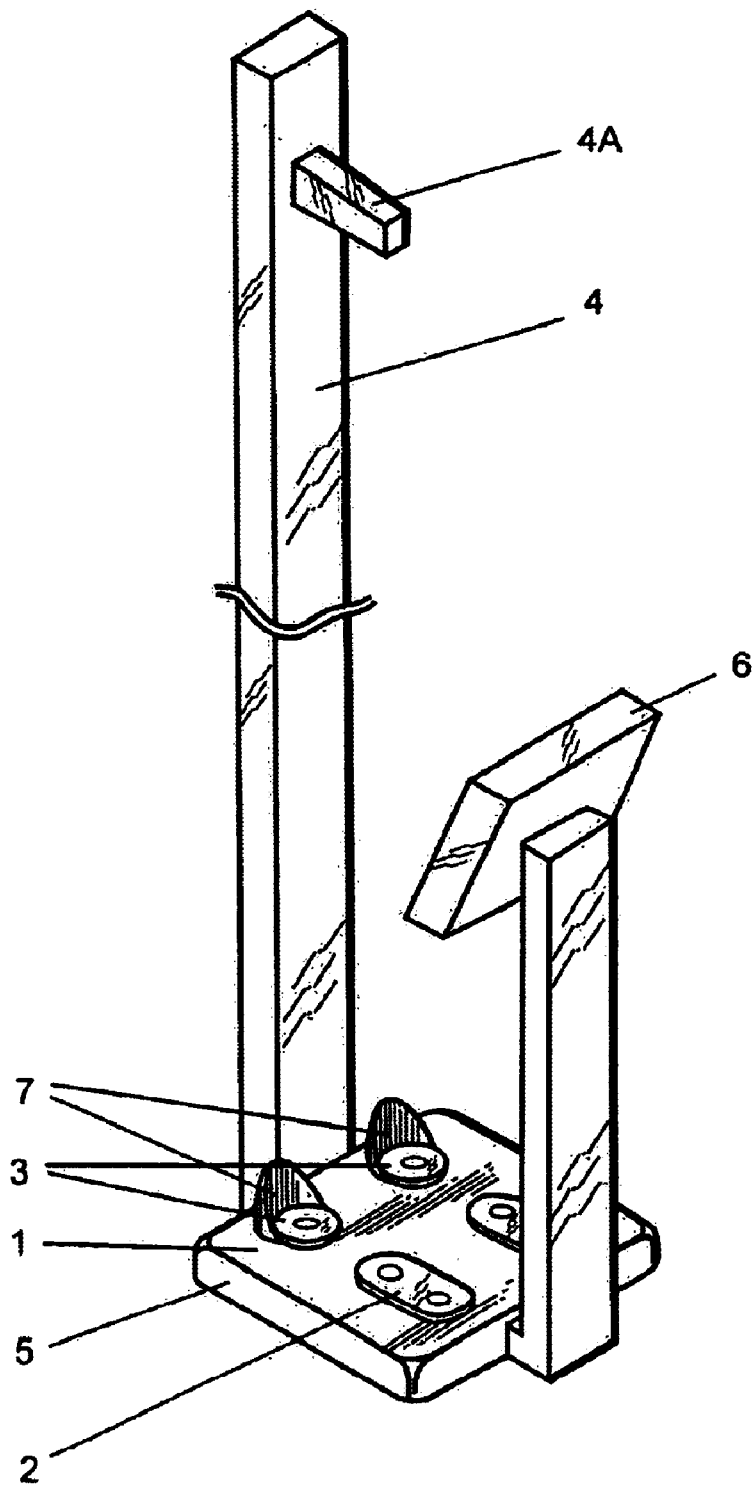
FIGS. 1–3 depict various views of a prior art body fat analyzer.
Figure 2:
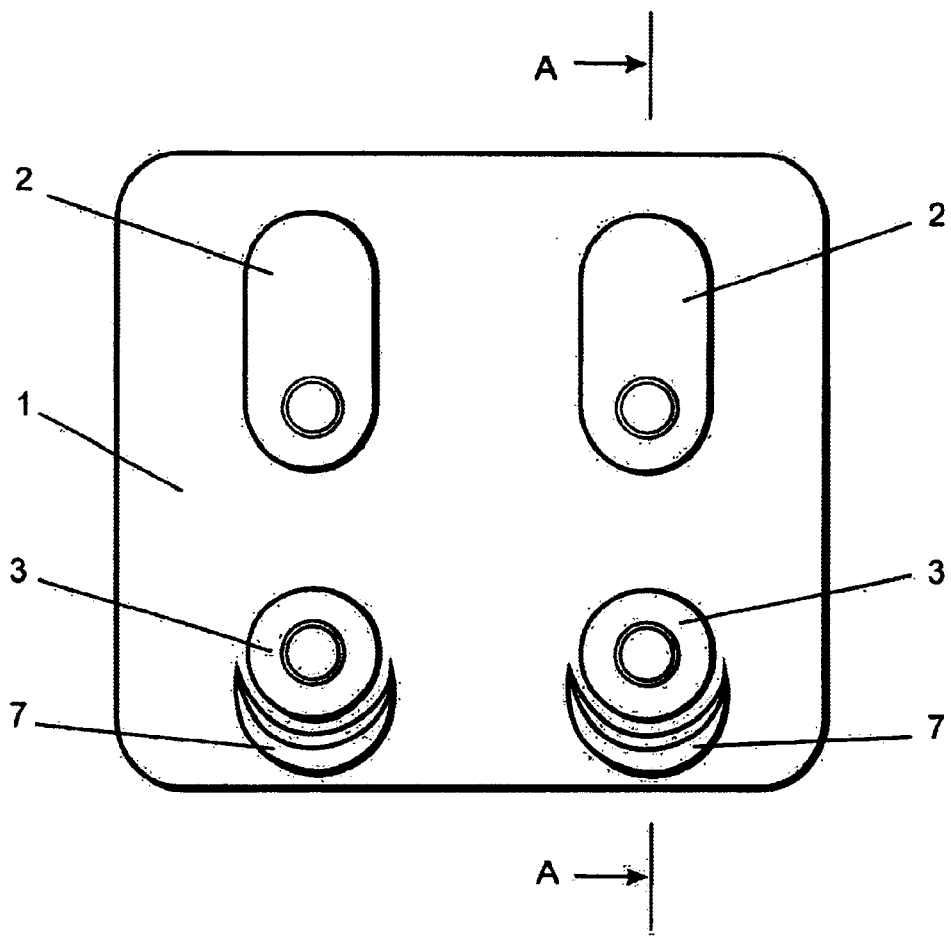
Figure 3:
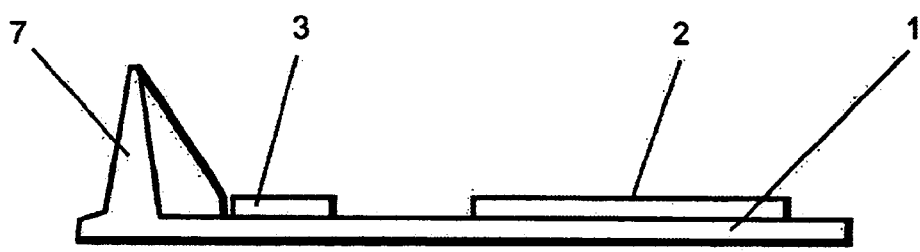
Figure 4:
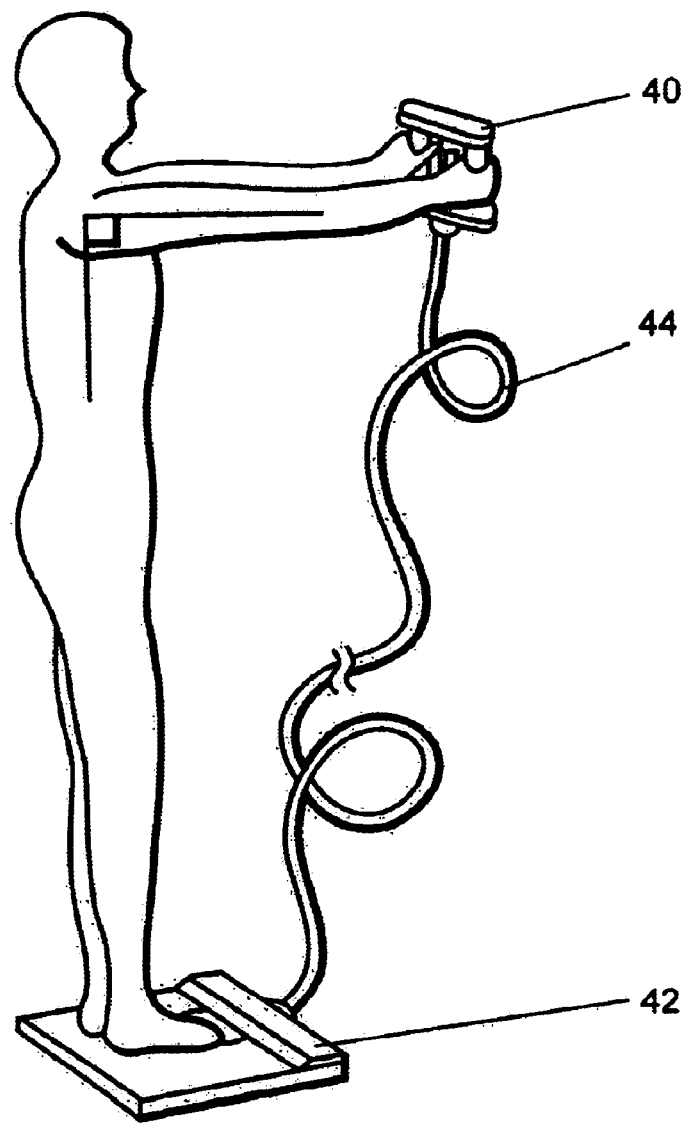
FIGS. 4–5 depict plan and sectional views of another prior art body fat analyzer.
Figure 5:
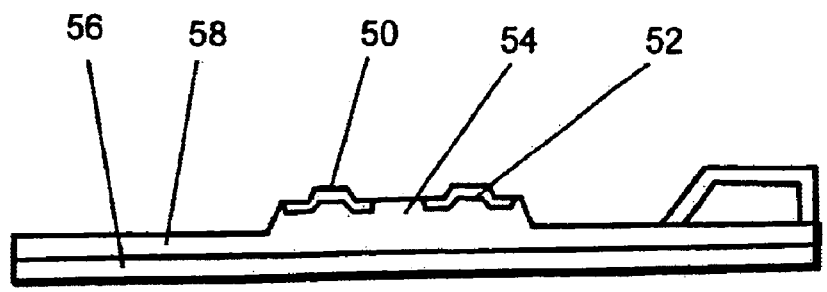
Figure 6:
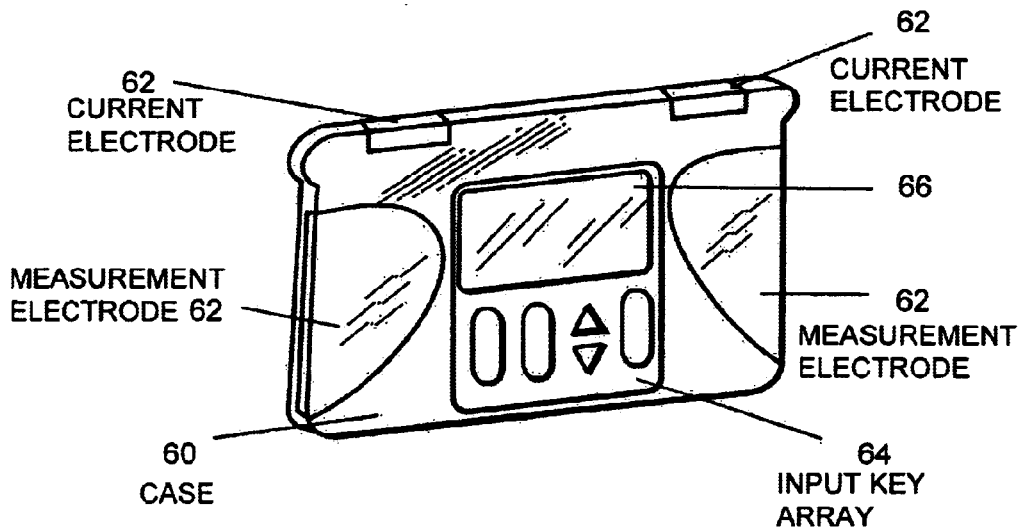
FIGS. 6–7 depict plan and sectional views of yet another prior art body fat analyzer.
Figure 7:
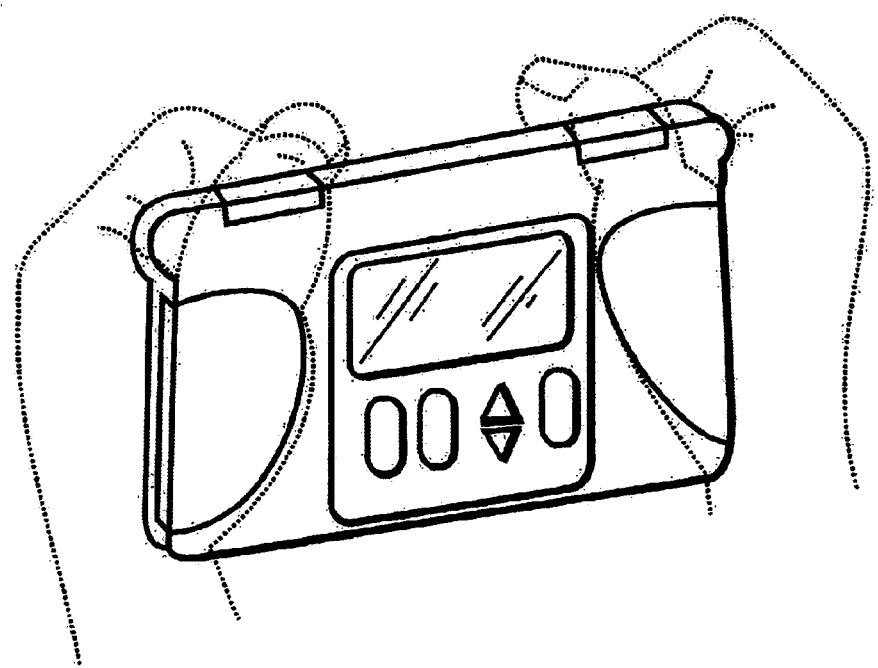
Figure 8:
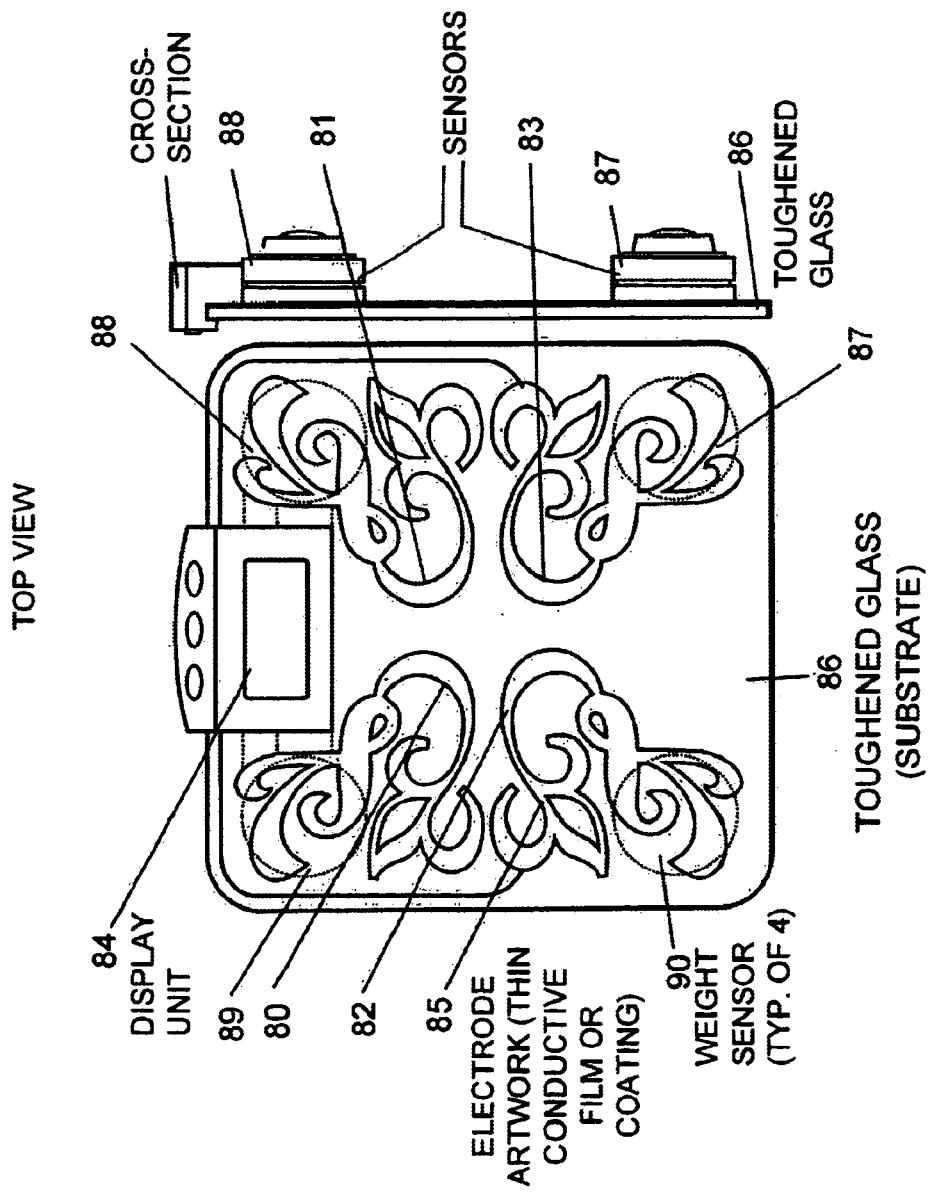
FIGS. 8–9 depict body fat analyzers in accordance with one embodiment of the present invention.

FIG. 8 illustrates a body fat analyzer in accordance with one embodiment of the present invention. It comprises substrate 86, two or more measurement electrodes 80–83, display unit 84, a measurement circuit (not shown) located within display unit 84, and weight sensors 87–90.

Suitable measurement circuits for use in bioelectrical-impedance-based body fat analyzers are well-known, and described, e.g., in the prior art references discussed above.

Substrate 86 may be composed of any non-conductive material capable of receiving a conductive-film layer. Suitable materials include, e.g., glass, ceramics, plastics, non-conductive stones, and insulators. Hardened glass, however, is a preferred material, because of its strength, rigidity, and aesthetic qualities.

Figure 9:
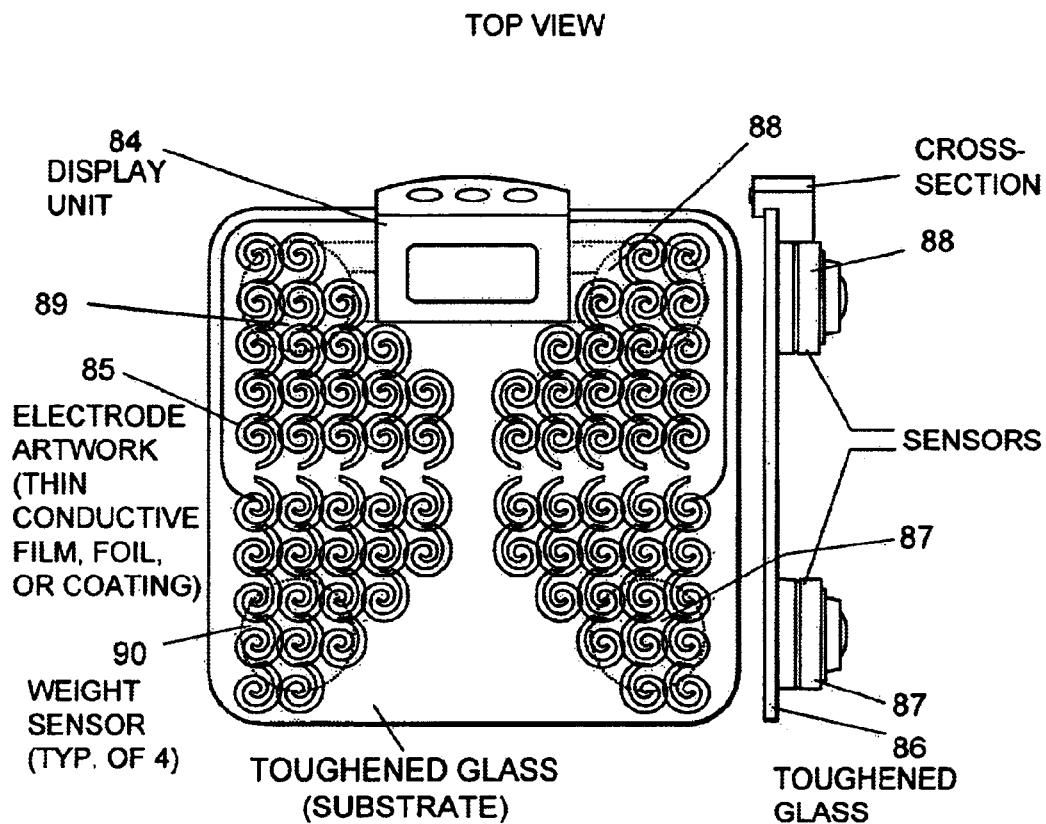

Electrodes 80–83 may be composed of any conductive material suitable for application as a conductive film on the substrate, using either thin-film or thick-film technology. A variety of metals, semiconductors, conductive inks and pastes, and TCMs such as zinc stannate ($ZnSnO_3$ and $Zn_2SnO_4$), fluorine-doped zinc oxide (ZnO:F), indium tin oxide ($In_2O$:Sn and $In_2O_3$:Sn), titanium nitride ($TiN_x$), and fluorine-doped tin oxide ($SnO_2$:F) have been successfully used to form conductive films in the manufacture of integrated circuits, thin-panel displays (including both liquid crystal displays and thin-film electroluminescent ("TFEL") displays), touch screens, and automobile glass, and are suitable for use with the present invention. TCMs are preferred materials for the electrodes, since their color and transparency can be controlled by the selection of the material or the addition of an ink to the material. It is thereby possible to produce a colored pattern on the substrate that can be very attractive. One such pattern is shown in FIG. 8; another is shown in FIG. 9.

The specific electrode material selected, however, will depend on process and customer requirements. Among the TCMs, for example, ZnO:F and $Cd_2SnO_4$ have the highest transparency. $In_2O$:Sn has the highest conductivity. TiN and $SnO_2$:F have a high mechanical durability. $SnO_2$:F has the best chemical durability. ZnO:F and TiN are the easiest to etch. Overall, $In_2O_3$:Sn has the highest conductivity, better transparency and easier etchability, and is therefore favored over other TCMs for use in patterning artwork electrodes for body fat analyzer applications.

The conductive-film electrodes may be produced on the substrate by known thin- and thick-film integration techniques, including adhesion, vapor deposition, cathodic arc deposition, sputtering, photolithography, spin-coating, and screen-printing. These techniques are well-known in the art. See, e.g., U.S. Pat. Nos. 6,315,874; 6,312,837; 5,122,391; and 6,146,765; and P. K. Vasudev, *Integrated Circuit Fabrication, in* ELECTRONIC ENGINEERING HANDBOOK 11.1 (Donald Christiansen et al. eds., 4th ed. 1997).

Two general methods of shaping the electrodes are available: (1) applying the electrode material uniformly onto the substrate, and then selectively removing it from selected areas of the substrate glass platform via sand-blasting, etching, laser patterning, grinding, etc.; or (2) by applying the electrode material only to selected portions of the substrate, as, for example, by (a) applying a mask layer before applying the conductive material to the substrate, and then removing the mask layer, or (b) screen-printing the conductive material through a patterned screen.

The thickness that is appropriate for the conductive-film electrodes is based on the stoichiometry of the substrate and the conductive-film material, the stresses placed on the material in the manufacturing process, the desired manufacturing time, the desired electrode resistance, and, in the case of transparent conductive materials, the desired transparency. Existing conductive-film conductors are typically between 20 nanometers to 5 micrometers thick. A thick electrode tends to be stronger and more resistant to stresses, have lower resistance, require a longer manufacturing time, and (in the case of a TCM) be less transparent. For example, a 100 ohm TCM coating will be approximately 20 nm thick, whereas a 10 ohm coating will be approximately 200 nm thick. Similarly, a 20 nm TCM layer will have transmittance around 90% and etching time less than 90 seconds, whereas a 200 nm thickness will have transmittance around 85% and etching time around 300 seconds. However, for body fat analyzers, the transmittance and etching time are less important than the electrode resistance. In a preferred embodiment, which has been reduced to practice, a TCM coating (of indium-tin-oxide) of 180 nm thickness was used, resulting in an electrode resistance of about 10 ohms but a transmittance of only about 85%.

Even this electrode resistance of 10 ohms can be very high in comparison with a typical body impedance, however, which can be as low as about 100 ohms. Accordingly, in the present invention, it is preferable to configure the measurement circuit such that it corrects for the electrode impedance, e.g., by comparing the impedance measured across the body with that measured across internal calibration impedances. By means of such a technique, which is now well-known in the body fat measurement art and described, e.g., in U.S. Pat. No. 5,611,351, a corrected body impedance value may be obtained that is independent of the impedance of the electrodes.

Preferably, the body fat analyzer in accordance with the invention further comprises a heating element in contact with the substrate and capable of warming the surface of the analyzer. This warming action renders the analyzer more comfortable to use and may increase the accuracy of the body fat measurement, since better capillary blood flow at the surface of the foot results. To control the heating element, a current source electrically connected to it is also required. Still more preferably, since the conductive-film electrodes themselves have a relatively high resistance, they may be used as the heating elements, and the current source may be included in the body fat measurement circuit.

In a further embodiment of the present invention, other circuitry used in body fat analyzers may be additionally provided on the substrate as integrated circuits. Such circuits may include, for example, a thin-panel display, a touch-switch keypad, and an electromagnetic shield positioned to protect the measurement circuit. Preferably, the measurement circuit itself is also integrated on the substrate.

Figure 10:
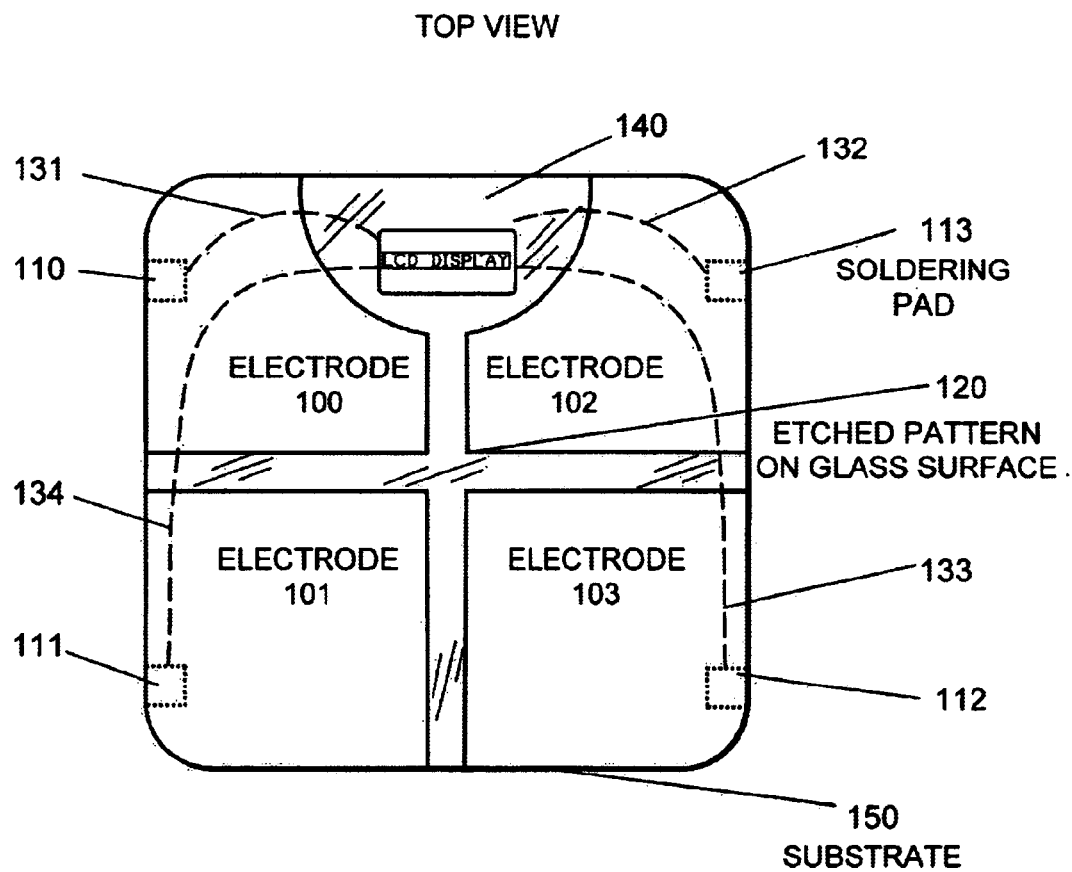
FIG. 10 depicts a body fat analyzer in accordance with another embodiment of the present invention.

Connections from the measurement circuit to the conductive-film electrodes may be made either via integrated conductive traces (as in FIGS. 8 and 9), or via wire conductors, as shown in FIG. 10. If the latter method is used, solder pads 110–113 may be provided that permit the conductors 131–134 to be easily soldered to the conductive-film electrodes. Such pads can be manufactured, e.g., by screen-printing solder paste at the desired locations and then heat-treating the paste at a temperature sufficient to allow it to dry or cure.

Solder pads 110–113 may be provided either (1) on the upper surface of electrodes 100–103 or (2) on the lower surface of substrate 150. If they are mounted on electrodes 100–103, conductors 131–134 are preferably routed from the measurement circuit below substrate 150 up around its edges to solder pads 110–113, respectively, without passing through perforations in the surface of substrate 150. If they are mounted on the lower surface of substrate 150, however, conductive traces must be provided from electrodes 100–103 to solder pads 110–113. These traces are preferably formed from the same material as that forming electrodes 100–103 and routed, as described above, around the edge of substrate 150 to the solder pads below. In this way, connections from the measurement circuit to the electrodes may be made without requiring holes or penetrations in substrate 150. It will be recognized that the resulting body fat analyzer will have enhanced water-resistant characteristics over existing body fat analyzers.

To further improve the water-resistance of the analyzer, a gasket may preferably be mounted around the edge of the substrate, which tends to keep water present on the top surface of the substrate from reaching its bottom surface. Suitably-shaped gaskets are commercially available and will not be further described herein.

The invention thus further includes a method of producing a body fat analyzer, comprising the steps of: (1) affixing at least two electrodes on the top surface of a substrate having top and bottom surfaces and an edge therebetween; and (2) electrically connecting to the electrodes a body fat measurement circuit mounted below the substrate, such that the top surface of the substrate remains intact, whereby water present thereon is prevented from reaching the circuit. Preferably, the connecting step includes the step of providing, for each electrode, a conductive path (e.g., a wire conductor or a conductive trace) from the substrate's top surface to its bottom surface via its edge. Finally, the method preferably includes the step of providing, near the edge of the substrate, a gasket that tends to keep water present on the top surface of the substrate from reaching the bottom surface of the substrate.

In summary, there has been disclosed a body fat analyzer having conductive-film electrodes that are integrated onto the surface of a suitable substrate, such as glass. A body fat analyzers produced in accordance with the invention has a number of advantages over existing body fat scales, including improved resistance to environmental pollutants, a reduced cost to manufacture, and an electrode pattern that permits a wide range of standing positions for the user.

It should be understood that the embodiments described herein are merely illustrative and not intended to limit the scope of the invention. For example, it will be recognized that the present invention is not limited only to body fat analyzers but is rather applicable to any biometric data acquisition device, as reflected in the claims below. Additionally, one skilled in the art may make various changes, rearrangements and modifications without substantially departing from the principles of the invention, which is limited only in accordance with the claims.

What is claimed is:

1. A biometric data acquisition assembly, comprising:
   a. a substrate;
   b. at least two conductive-film electrodes, each having an impedance, formed from a conductive material integrated on said substrate and capable of contacting an object having a biometric electrical characteristic to be measured;
   c. a biometric data acquisition circuit electrically connected to said electrodes and configured to measure a biometric electrical characteristic of the object via said conductive-film electrodes; and
   d. an internal calibration impedance that corrects for the impedances of the electrodes electrically connected to the biometric data acquisition circuit to enable correcting the biometric electrical characteristic value such that it is independent of the impedance of the electrodes.

2. The assembly of claim 1, wherein said substrate is one of a glass, a ceramic, a plastic, a non-conductive stone, and an insulator.

3. The assembly of claim 1, wherein said conductive material is one of a transparent conductive material, a metal, a semiconductor, a conductive ink, and a conductive paste.

4. The assembly of claim 3, wherein said transparent conductive material is one of zinc stannate, fluorine-doped zinc oxide, indium tin oxide, titanium nitride, and fluorine-doped tin oxide.

5. The assembly of claim 1, wherein said electrodes are no more than 5 micrometers thick.

6. The assembly of claim 1, wherein said electrodes are between 20 nanometers to 5 micrometers thick.

7. The assembly of claim 1, wherein said conductive-film electrodes are integrated on the substrate by one or more of the following thin- and thick-film integration techniques: adhesion, vapor deposition, cathodic-arc deposition, sputtering, photolithography, spin coating, and screen printing.

8. A biometric data acquisition assembly, comprising:
   a. a substrate;
   b. at least two conductive-film electrodes, each having an impedance, formed from a conductive material integrated on said substrate and capable of contacting an object having a biometric electrical characteristic to be measured;
   c. a biometric data acquisition circuit electrically connected to said electrodes and configured to measure a biometric electrical characteristic of the object via said conductive-film electrodes;
   d. an internal calibration impedance that corrects for the impedances of the electrodes electrically connected to the biometric data acquisition circuit to enable correcting the biometric electrical characteristic value such that it is independent of the impedance of the electrodes;
   e. a heating element formed by one or more of said electrodes in contact with said substrate; and
   f. a current source electrically connected to said heating element such that current may flow through it;
   whereby the current supplied by said current source causes said heating element to warm said substrate.

9. The assembly of claim 8, wherein said biometric data acquisition circuit comprises said current source.

10. A biometric data acquisition assembly, comprising:
    a. a substrate;
    b. at least two conductive-film electrodes, each having an impedance, formed from a conductive material integrated on said substrate and capable of contacting an object having a biometric electrical characteristic to be measured;
    c. a biometric data acquisition circuit electrically connected to said electrodes and configured to measure a biometric electrical characteristic of the object via said conductive-film electrodes;
    d. an internal calibration impedance that corrects for the impedances of the electrodes electrically connected to the biometric data acquisition circuit to enable correcting the biometric electrical characteristic value such that it is independent of the impedance of the electrodes;
    e. a thin-panel display integrated on said substrate,
    f. a touch-switch keypad integrated on said substrate, and
    g. an electromagnetic shield integrated on said substrate and positioned such that said biometric data acquisition circuit is at least partially protected from electromagnetic radiation.

11. A biometric data acquisition assembly, comprising:
    a. a substrate;
    b. at least two conductive-film electrodes, each having an impedance, formed from a conductive material integrated on said substrate and capable of contacting an object having a biometric electrical characteristic to be measured;
    c. a biometric data acquisition circuit electrically connected to said electrodes and configured to measure a biometric electrical characteristic of the object via said conductive-film electrodes, wherein said biometric data acquisition circuit is also integrated on said substrate; and
    d. an internal calibration impedance that corrects for the impedances of the electrodes electrically connected to the biometric data acquisition circuit to enable correcting the biometric electrical characteristic value such that it is independent of the impedance of the electrodes.

* * * * *